United States Patent [19]

Schaefer et al.

[11] Patent Number: 4,871,876

[45] Date of Patent: Oct. 3, 1989

[54] PREPARATION OF 4,4′ DICHLORODIPHENYL SULFONE

[75] Inventors: Gerhard Schaefer, Heidelberg; Peter Neumann, Wiesloch, both of Fed. Rep. of Germany

[73] Assignee: Dresser Industries, Inc., Dallas, Tex.

[21] Appl. No.: 147,759

[22] Filed: Jan. 25, 1988

[30] Foreign Application Priority Data

Feb. 17, 1987 [DE] Fed. Rep. of Germany ....... 3704932

[51] Int. Cl.$^4$ .......................................... C07C 147/06
[52] U.S. Cl. ..................................................... 568/34
[58] Field of Search ......................................... 568/34

[56] References Cited

U.S. PATENT DOCUMENTS

| | | | |
|---|---|---|---|
| 3,701,806 | 10/1972 | Keogh et al. | 568/34 |
| 3,855,312 | 12/1974 | Horner | 568/34 |
| 4,172,852 | 10/1979 | Ark et al. | 568/34 |
| 4,558,161 | 12/1985 | Morita et al. | 568/34 |

FOREIGN PATENT DOCUMENTS

| | | |
|---|---|---|
| 62736 | 10/1982 | European Pat. Off. . |
| 895473 | 5/1962 | United Kingdom . |
| 1572916 | 8/1980 | United Kingdom . |
| 2135666 | 9/1984 | United Kingdom . |

OTHER PUBLICATIONS

J. Am. Chem. Soc., 76 (1954), p. 5491, P. Kovacic et al.

*Primary Examiner*—Mary E. Ceperley

[57] ABSTRACT

A process for the preparation of 4,4-dichlorodiphenyl sulfone by heating a mixture of (a) chlorobenzene, (b) chlorosulfonic acid or sulfur trioxide, and (c) thionyl chloride or phosgene to temperatures up to 220° C., more than the stoichiometric amount (based on the amount of chlorobenzene) of chlorosulfonic acid or sulfur trioxide and less than the stoichiometric amount of thionyl chloride or phosgene being employed.

8 Claims, No Drawings

PREPARATION OF 4,4' DICHLORODIPHENYL SULFONE

The present invention relates to a novel process for the preparation of 4,4'-dichlorodiphenyl sulfone.

4,4'-Dichlorodiphenyl sulfone is an important intermediate; it is used mainly for the preparation of aromatic polysulfones and the synthesis of bis(4-aminophenyl) sulfone, which is employed in the treatment of leprosy and for curing epoxy resins. 4,4-Dichlorodiphenyl sulfone for these applications must be of high purity.

4,4-Dichlorodiphenyl sulfone can be prepared, for example, from chlorobenzene by treating it with a mixtur of sulfur trioxide and dimethyl or diethyl pyrosulfate, as in the process described in German Pat. No. 1 087 592. Synthesis from chlorobenzene and chlorobenzenesulfonic acid is described in German Published Application No. 2 252 571; for this temperatures of from 220° C. to 260° C. are required, so that it is necessary to work at elevated pressures.

The best-known method for preparing 4,4-dichlorodiphenyl sulfone is by the Friedel-Crafts reaction between 4,4-dichlorobenzenesulfochloride and chlorobenzene, with iron(III) chloride, for instance, as catalyst. This process is described in, for instance, German Pat. No. 2 704 972, and the use of iron(III) chloride is a disadvantage here. The conversion to the sulfone is carried out with chlorobenzene as solvent at about 140° C.; it is known from *J. Am. Chem. Soc.*, 76, 5491 (1954) that at this temperature iron(III) chloride also promotes the chlorination of chlorobenzene, so that the chlorobenzene used as solvent and recycled contains a considerable proportion of dichlorobenzenes; since these also form sulfones with chlorobenzenesulfochloride, they necessitate expensive purification.

If the reaction is carried out as a single-stage reaction, starting from chlorobenzene and without the isolation of the intermediate 4-chlorobenzenesulfochloride, care must be taken that no sulfonic acid, thionyl chloride, or sulfur chlorides (these occur as impurities in thionyl chloride) remain in the reaction mixture: free sulfonic acid deactivates the catalyst, thionyl chloride and sulfur chlorides cause unwanted side products.

The matter is aggravated by the necessity of adding dimethylformamide, to ensure complete conversion of 4-chlorobenzenesulfonic acid to the sulfochloride by means of thionyl chloride, since the carcinogenic dimethylcarbamoyl chloride is formed as a by-product. furthermore, the iron(III) chloride must be removed from the reaction product by hydrolysis; this gives a very corrosive medium, which places high requirements on the engineering materials used, and considerable quantities of chlorobenzene get into the water,whichmeans that the waste water must be treated.

The object of the invention was to provide a process for the preparation of 4,4-dichlorodiphenyl sulfone from chlorobenzene,sulfur trioxide or chlorosulfonic acid, and thionyl chloride or phosgene that does not require the addition of the catalysts iron(III) chloride and N,N-dimethylformamide. Furthermore, 4,4-dichlorodiphenyl sulfone was to be obtained very pure and in high yield.

We have found that this object is achieved if in the preparation of 4,4-dichlorodiphenyl sulfone by heating a mixture of (a) chlorobenzene, (b) chlorosulfonic acid or sulfur trioxide, and (c) thionyl chloride or phosgene to temperatures up to 220° C. more than the stoichiometric amount (based on the amount of chlorobenzene) of chlorosulfonic acid or sulfur trioxide and less than the stoichiometric amount of thionyl chloride or phosgene are taken.

It is known that equal amounts of (a), (b), and (c) react to form chlorobenzenesulfonic acid at first, this being then chlorinated to chlorobenzenesulfonic acid chloride, which requires the same amount of chlorobenzene again for the formation of dichlorodiphenyl sulfone.

Because the non-stoichiometric proportions of the starting compounds the novel process leads to the formation of a slight excess of chlorobenzenesulfonic acid, which catalyzes the conversion of the chlorobenzenesulfonic acid chloride to the sulfone. In the conventional process an excess of chlorobenzene is employed, and the temperatures necessary for the formation of the sulfone are not attained; in the novel process it is ensured that reaction temperatures of from 165° C. to 220° C. are attained. The final product is a melt consisting of isomeric dichlorodiphenyl sulfones and chlorobenzenesulfonic acid.

In the novel process particularly favorable results are obtained if the amounts are in the proportions 1 mol of chlorobenzene to from 0.51 mol to 0.63 mol—preferably from 0.54 mol to 0.59 mol—of chlorosulfonic acid or sulfur trioxide to from 0.49 mol to 0.37 mol—preferably from 0.46 mol to 0.41 mol—of thionyl chloride or phosgene.

The mixture of starting compounds for the formation of 4,4-dichlorodiphenyl sufone is heated to from 165° C. to 220° C., preferably to from 185° C. to 200° C. It is expedient to add up to 40% of the total amount of chlorobenzene required while the mixture is being heated up. The reaction time is roughly from 1 h to 6 h.

The end of the reaction can be found by determining the chlorobenzenesulfonic acid chloride content of the reaction mixture. This analysis can be carried out by thin-layer chromatography, gas chromatography, or high-pressure liquid chromatography, for example. If gas chromatography is employed the amount of chlorobenzene added can be monitored, and adjusted so that at the end of the reaction the mass fractions of chlorobenzene and chlorobenzenesulfonic acid chloride are well below 1%,thus ensuring that all the chlorobenzene employed has been converted.

The melt, which contains isomeric dichlorodiphenyl sulfones in the approximate proportions of 91% of 4,4'-isomer, 6% of 3,4'-isomer, and 3% of 2,4''-isomer, can be treated by, for instance, methods knownperse. The required 4,4'-isomer is however obtained very pure and in high yield by a novel, particularly advantageous embodiment of the novel process: the melt is diluted with alcohols or aromatic solvents, under pressure if needed, thus causing the 4,4-dichlorodiphenyl sulfone to precipitate. Suitable alcohols are alkanols of from 1 to 4 carbon atoms;suitable aromatic solvents are chlorobenzene and toluene, for instance. Particularly good results are obtained withmethanol or chlorobenzene as precipitant. In a preferred procedure the melt is diluted by pouring it into methanol, the temperature being chosen so that a pressure of about from 4 bar to 6 bar is obtained.

The solvent used for precipitation can be easily recovered from the supernatant liquor by distillation. The chlorobenzenesulfonic acid remaining in the residue from distillation can be fed back for use as catalyst in the reaction. If chlorobenzene is used as precipitant the supernatant liquor can be returned direct for re-use in the reaction; since it contains the amount of chlorobenzenesulfonic acid needed for catalysis subsequent charges should contain stoichiometric amounts of thionyl chloride and chlorosulfonic acid.

4,4-Dichlorodiphenyl sulfone is obtained in high yield and purity by the novel process, which can also be carried out continuously. The fact that conversion to chlorobenzenesulfonic acid chloride does not have to be complete is a considerable advantage, since there is thus no need to add dimethylformamide to catalyze this reaction. Another favorable point is that the purity of the thionyl chloride does not have tosatisfy high requirements respecting sulfur chlorides, since these do not lead to the formation of undesirable by-products (such as dichlorodiphenyl sulfides) under the conditions of the reaction.

EXAMPLE 1

629 g (5.4 mol) of chlorosulfonic acid and 547.4 g (4.6 mol) of thionyl chloride are added to 1125 g (10 mol) of chlorobenzene at from 55° C. to 65° C. After evolution of hydrogen chloride has stopped the reaction mixture is heated, and at 135° C. it begins to boil,with evolution of hydrogen chloride. After 4–5 h the reflux diminishes noticeably and the internal temperature rises to 195° C. Once this temperature is reached there is no detactable reflux of chlorobenzene. Gas-chromatographic analysis of the mixture in the vessel shows that almost all the chlorobenzenesulfonic acid chloride has been converted to the sulfone: less than 1% remains.

The whole charge is cooled to 150° C. and stirred into 1 liter of methanol, with evaporative cooling. After cooling the precipitate is filtered off and washed withmethanol. 944 g (71.5% yield, based on the amount of thionyl chloride) of 4,4'-dichlorodiphenyl sulfone with a melting point of 149°–150° C. is obtained. Gas-chromatographic analysis of the product gives not less than 99.7% 4,4'isomer, less than 0.1% 3,4'-isomer, and up to 0.2% 2,4'-isomer.

EXAMPLES 2 to 7

Theprocedure given in Example 1 is repeated with the amounts of starting compounds given in the following table, which also gives the yields and purities of the 4,4-dichlorodiphenyl sulfone obtained.

| Ex. No. | Amount of compound/mol | | | Reaction time/h | Yield/% based on | | 4,4'-mass fraction/% |
|---|---|---|---|---|---|---|---|
| | ClSO$_3$H | SOCl$_2$ | C$_6$H$_5$Cl | | SOCl$_2$ | C$_6$H$_5$Cl | |
| 1 | 5.4 | 4.6 | 10 | 18 | 71.5 | 63.5 | 99.7 |
| 2 | 5.2 | 4.8 | 10 | 32 | 56.3 | 53.6 | 99.5 |
| 3 | 5.4 | 4.6 | 10 | 26 | 62.2 | 57.8 | 99.6 |
| 4 | 5.5 | 4.5 | 10 | 20 | 70.8 | 64.3 | 99.6 |
| 5 | 5.7 | 4.3 | 10 | 17 | 72.1 | 62.6 | 99.7 |
| 6 | 5.8 | 4.2 | 10 | 15 | 73.4 | 61.2 | 99.7 |
| 7 | 6.0 | 4.0 | 10 | 14 | 74.5 | 59.6 | 99.7 |

EXAMPLE 8

629 g (5.4 mol) of chlorosulfonic acid and 547.4 g (4.6 mol) of thionyl chloride are added to 787.5 g (7 mol) of chlorobenzene at from 55° C. to 65° C., and the mixture is heated rapidly to 185° C. There is no appreciable reflux. Heating is continued, and when the temperature reaches 195° C. 337.5 g (3 mol) of chlorobenzene is added at such a rate that the temperature of the mixture does not fall appreciably. Subsequent treatment of the charge is as described in Example 1, 953 g (72.2% yield, based on the amount of thionyl chloride) of 4,4-dichlorodiphenyl sulfone of melting point 149°–150° C. is obtained.

EXAMPLES 9–15

The procedure is as in Example 8, except that the 337.5 g of chlorobenzene is added at the temperatures given in the following table.

| Ex. No. | C$_6$H$_5$Cl added at: temp./°C. | Reaction time/h | ClC$_6$H$_4$SO$_2$Cl mass fraction/% (GC) | Yield/% based on SOCl$_2$ | Color of product |
|---|---|---|---|---|---|
| 8 | 195 | 17 | 0.3 | 72.2 | white |
| 9 | 200 | 16 | 0.2 | 73.0 | white |
| 10 | 210 | 15.5 | 0.2 | 73.3 | gray |
| 11 | 220 | 14.5 | not detected | 73.5 | gray |
| 12 | 190 | 18 | 0.3 | 72.1 | white |
| 13 | 185 | 19 | 1 | 70.6 | white |
| 14 | 175 | 25 | 3 | 68.8 | white |
| 15 | 165 | 40 | 8 | 62.3 | white |

EXAMPLE 16

The filtrate from Example 1 is freed from methoanol by distillation, the residue is returned to the reaction vessel, and 562.5 g (5 mol) of chlorobenzene is added. chlorobenzenesulfonic acid chloride is formed by adding 476 g (4 mol) of chlorosulfonic acid and 466 g (4 mol) of thionyl chloride, the mixture is heated to 195° C., and 337.5 g (3 mol) of chlorobenzene is added at such a rate that the temperature does not fall. the charge is subsequently treated as described in Example 1, giving 850 g (74% yield) of dichlorodiphenyl sulfone of melting point 149°–150° C. Gas-chromatographic analysis of the product gives 99.6% 4,4'-isomer, 0.3% 2,4'-isomer, and 0.1% 3,4'-isomer.

EXAMPLE 17

Molten reaction mixture obtained by proceeding as in Example 8 is poured into a pressure vessel containing 1.5 liters of methanol. The mixture is heated to from 110° C. to 115° C., raising the pressure to 4.5 bar, and stirred for another hour. After cooling,filtration, and washing with methanol 931 g dichlorodiphenyl sufone containing 99.8% 4,4'-isomer and not more than 0.1% each of 2,4'- and 3,4'-isomers is obtained.

We claim:
1. A process for the preparation of 4,4-dichlorodiphenyl sulfone which comprises heating a mixture of (a) chlorobenzene, (b) chlorosulfonic acid or sulfur trioxide, and (c) thionyl chloride or phosgene to provide a molten reaction mixture at temperatures of from 165° C. upto 220° C., employing more than the stoichiometric amount, based on te amount of chlorobenzene, of chlor- osulfonic acid or sulfur tioxide and less than the stoichiometric amount of thionyl chloride or phosgene.

2. A process as claimed in claim 1 wherein the amounts are in the proportions 1 mol of chlorobenzene to from 0.51 mol to 0.63 mol of chlorosulfonic acid or sulfur trioxide to from 0.49mol to 0.37 mol of thionylchloride or phosgene.

3. A process as claimed in claim 1 wherein the amounts are in the proportions 1 mol of chlorobenzene to from 0.54 mol to 0.59 mol of chlorosulfonic acid or sulfur trioxide to from 0.46 mol to 0.41 mol of thionyl chloride or phosgene.

4. A process as claimed in claim 1 wherein part of the amount of chlorobenzene, but not more than one half, is added to the reaction mixture as it is being heated up to a reaction temperature of from 165° to 220° C., and the remaining part is added after reaching the reaction temperature.

5. A process as claimed in claim 1 wherein alcohols or aromatic solvents are added to the melt obtained through thereaction and the 4,4′-dichlorodiphenyl sulfone that precipitates on cooling is separated.

6. A process as claimed in claim 5 wherein the alcohols are alkanols of from 1 to 4 carbon atoms and the aromatic solvent is chlorobenzene or toluene.

7. A process as claimed in claim 5 wherein the residue left after removal of the 4,4-dichlorodiphenyl sulfone and recover of the solvent yb distillation is re-used for a reaction as claimed in claim 1 after the three starting compounds have been added to it.

8. A process as claimed in claim 5 wherein chlorobenzene is added to the melt and the supernatant liquor left after the 4,4-dichlorodiphenyl sulfone has been removed is re-used for a reaction as claimed in claim 1 after chlorosulfonic acid or sulfur trioxide and thionyl chloride or phosgene have been added to it.

* * * * *

UNITED STATES PATENT AND TRADEMARK OFFICE
CERTIFICATE OF CORRECTION

PATENT NO. : 4,871,876

DATED : October 3, 1989

INVENTOR(S) : Gerhard Schaefer and Peter Neumann

It is certified that error appears in the above-identified patent and that said Letters Patent is hereby corrected as shown below:

On the title page, item [73] Assignee:, change "Dresser Industries, Inc., Dallas, Tex., to: --BASF Aktiengesellschaft, Ludwigshafen, Fed. Rep. of Germany--.

In Claim 1, at line 6: change "upto" to read --up to--, and at line 7, change "te" to read --the--.

In Claim 5, at line 3, change "thereaction" to read --the reaction--.

In Claim 7, at line 3, change "recover" to read --recovery-- and change "yb" to read --by--.

Signed and Sealed this

Seventh Day of August, 1990

Attest:

HARRY F. MANBECK, JR.

*Attesting Officer*  *Commissioner of Patents and Trademarks*